United States Patent [19]

Tilcock et al.

[11] Patent Number: 4,923,854
[45] Date of Patent: May 8, 1990

[54] SOLUBILIZATION OF HYDROPHOBIC MATERIALS USING LYSOPHOSPHOLIPID

[75] Inventors: Colin P. S. Tilcock; Pieter R. Cullis; Michael J. Hope, all of Vancouver, Canada; Andrew S. Janoff, Yardley, Pa.

[73] Assignee: The Liposome Company, Inc., Princeton, N.J.

[21] Appl. No.: 821,366

[22] Filed: Jan. 22, 1986

[51] Int. Cl.$^5$ .................. A61K 31/685; A01N 57/26; A01N 43/16
[52] U.S. Cl. ...................................... 514/78; 424/450
[58] Field of Search ........................... 514/78; 424/450

[56] References Cited

U.S. PATENT DOCUMENTS

| | | | |
|---|---|---|---|
| 3,752,886 | 8/1973 | Munder et al. | 514/78 |
| 4,239,754 | 12/1980 | Sache et al. | 514/78 |
| 4,263,286 | 4/1981 | Nakajima et al. | 514/78 |
| 4,372,949 | 2/1983 | Kodama et al. | 424/199 |
| 4,622,219 | 11/1986 | Haynes | 514/817 |

FOREIGN PATENT DOCUMENTS

| | | | |
|---|---|---|---|
| 88046 | 9/1983 | European Pat. Off. | 424/450 |
| 179114 | 11/1982 | Japan | 514/162 |
| 163315 | 9/1984 | Japan | 514/274 |
| 968 | 3/1985 | World Int. Prop. O. | 424/450 |

OTHER PUBLICATIONS

The Merck Index, 10th Ed., (1983), #1937 Cephalins; #7395, Plasmalogens.
Tilcock et al., The Polymorphic Phase Behavior and Miscibility Properties of Synthetic Phosphatidylethanolamines, 1982, BBA., 684, pp. 212-218.
Cullins et al., The Polymorphic Phase Behavior of Phosphatidylethanolamines of Natural and Synthetic Origin, 1978, BBA., 513, pp. 31-42.
Cullis et al., Polymorphic Phase Behavior of Lipid Mixtures as Detected by $^{31}$P-NMR. 1978, BBA 507, pp. 207-218.
Madden et al., Stabilization of Bilayer Structure for Unsaturated Phosphatidylethanolamines by Detergents. 1982, BBA, 684, pp. 149-153.
Bentz et al., On the Correlation Between $H_{II}$Phase and the Contact-Induced Destabilization of Phosphatidylethanolamine-Containing Membranes, 1985, Proc. Natl. Acad. Sci. U.S.A., 82, pp. 5742-5745.
Peterson et al., Characterization of the Interactions Between Lysophosphatides, Triton X-100, and Sarcoplasmic Retriculum, 1977, Arch. Biochem. Biophys. 179, pp. 218-228.

Primary Examiner—Joseph A. Lipovsky
Attorney, Agent, or Firm—Allen Bloom, Esq.; Catherine L. Kurtz

[57] ABSTRACT

A method and composition are described for the solubilization of hydrophobic materials using a lysophospholipid. The method includes drying a composition comprising a hydrophobic material-solubilizing effective amount of phospholipid from organic solvent and hydrating the resulting film with an aqueous medium at either a pH of between about 8.5 and about 14.0, or at pH 7.0 followed by reduction of the temperature to less then 0° C.

99 Claims, 5 Drawing Sheets

FIG. 1

$^{31}$P-NMR SPECTRA OF LOPE AT pH 7

FIG. 2

$^{31}$P-NMR SPECTRA OF pH DEPENDENT POLYMORPHIC PHASE BEHAVIOR OF LOPE

FIG. 3

31P-NMR SPECTRA OF TEMPERATURE-DEPENDENT POLYMORPHIC PHASE BEHAVIOR OF sn-1-18:2$_{cis}$-PE AND sn-1-18:3$_{cis}$-PE

SOLUBILIZATION OF HYDROPHOBIC MATERIALS USING LYSOPHOSPHOLIPID

BACKGROUND OF THE INVENTION

The present invention is directed to the field of solubilization of hydrophobic materials. More particularly, the invention describes the use of certain lysophospholipids as solubilizers and non-toxic delivery vehicles.

The solubilization of hydrophobic materials, particularly bioactive materials, is typically achieved by the use of surfactants such as sodium deoxycholate or propylene glycol. Such surfactants, due to their detergent properties, are biologically incompatible and toxic due to their lytic effects on cells. It would, therefore, be desirable to employ a naturally occurring substance without toxic properties as a surfactant for pharmaceutical use.

Lysophospholipids have heretofore been improbable candidates for pharmaceutical excipients due to their lytic effects on cells. We describe a method and compositions for a lysophosphatide, specifically lysophosphatidylethanolamine, alone and in combination with an unsaturated phospholipid for solubilizing hydrophobic materials.

Peterson et al., *Arch Biochem Biophys*, 179, 218–228 (1977), observed lysophosphatidylethanolamine's (LPE) properties, as an ATPase inhibitor in biomembranes; these effects probably due to LPE intrusion into the membrane around the enzyme resulting in a less fluid lipid environment. Lysophospholipid suspensions were mixed with fractions of sacroplasmic spectrophotometric assay. LPE, however, unlike lysophosphatidylcholine, never solubilized biomembrane at any concentration.

The present invention exploits the pH and temperature dependent phase transitions of lysophosphatidylethanolamines to result in micellar solubilization of hydrophobic materials and delivery of a non-toxic product.

SUMMARY OF THE INVENTION

The present invention describes solubilization of Hydrophobic substances using LPE alone or LPE in combination with an unsaturated phospolipid.

The LPE's of the present invention have the formula or wherein R is a hydrocarbon chain having between about 11 and 21 carbon atoms and between about 0 to 6 double bonds, preferably 13–19 carbon atoms, and more preferably 15–17 carbon atoms and 1–3 double bonds. A preferred LPE is that wherein $RCO_2$ is 1-oleoyl, as in formula I above, where the oleoyl group is bound to the 1 carbon atom.

A phospholipid is a glycerol molecule having one hydroxy esterified to phosphoric acid which is further esterified to an alcohol component; and the other glycerol hydroxyls are esterified to carboxylate fatty acid chains. The unsaturated phospholipids used in the present invention contain at least one fatty acid chain of between about 12 and 22 carbon atoms and about 1 to 6 double bonds, preferably about 16 to 20 carbon atoms and about 1 to 3 double bonds. The second fatty acid chain contains about 12 to 22 carbon atoms and about 0 to 6 double bonds, preferably about 14 to 18 carbon atoms and about 0 to 2 double bonds, more preferably 0 or 1 double bonds. Suitable phospholipids include, but are not limited to, derivatives of phosphatidylserine, phosphatidylethanolamine, phosphatidylinositol or phosphatidylcholine. Preferred unsaturated phospholipids include egg phosphatidylcholine, soy phosphatidylcholine or dioleoylphosphatidylcholine.

The lysophospholipid, LPE, alone or in combination with a phospholipid, is mixed with the hydrophobic material in an aqueous medium at a temperature of between about 1° C. and about 90° C., and at pH between about 8.5 and 14.0, preferably about 25° C. and about pH 8.5. Alternatively, a more highly unsaturated LPE may be used; in this case, the hydrophobic material may be mixed with the lipid and aqueous medium at a temperature of between about 0° C. and about 90° C., preferably about 25° C. and at about pH 7.0. The temperature of the suspension is then reduced to below 0° C. The hydrophobic material can comprise bioactive agents including, but not limited to, drugs, hormones, proteins, dyes, vitamins or imaging agents. The aqueous medium can comprise a buffer system such as borate or N-2-hydroxyethyl piperazine-N'-2-ethane sulfonic acid (HEPES). The resulting suspension may be passed under pressure through a filter system such as stacked polycarbonate filters and may be sonicated to further disperse the hydrophobic material.

DETAILED DESCRIPTION OF THE INVENTION 1-oleoyl lysophosphatidylethanolamine may be expressed as wherein R is the oleoyl group attached to the carbon in the 1-position, as labeled [1], thus 1-oleoyl. The (OH) group is located on the [2] carbon. This lipid may be further expressed as sn-1-18:$1_{cis}$-PE, denoting the 18 carbon composition of the oleoyl group, followed by a number denoting the number of double bonds, in the case 1 double bond in the cis configuration. As a further illustration of the nomenclature, for example, more highly unsaturated LPE's, wherein R is in the 1-position and has 2 or 3 double bonds and 17 carbon atoms; are expressed as sn-1-18:$2_{cis}$-PE and sn-1-18:$3_{cis}$-PE, respectively. The carboxylate carbon atom is the 18th carbon atom.

Figure 1:
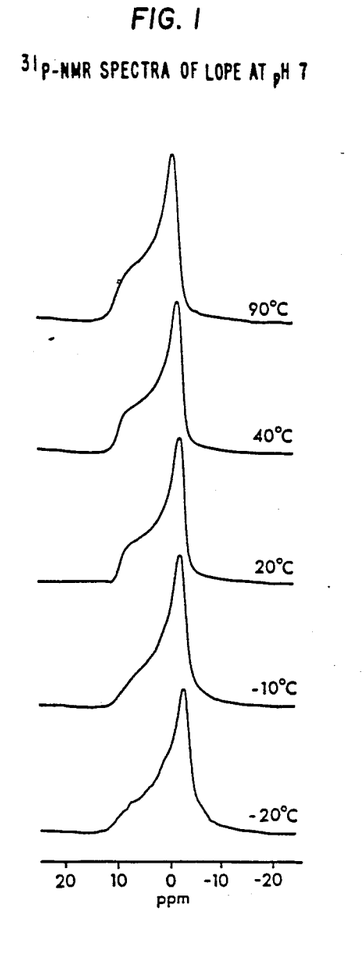
FIG. 1 are 81 MHz $^{31}$P-NMR spectra of aqueous dispersions of 1-oleoyl lysophosphatidylethanolamine (LOPE, or sn-1-18:$1_{cis}$-PE) at pH 7.0 between 31 20° C. and 90° C.
Figure 2:
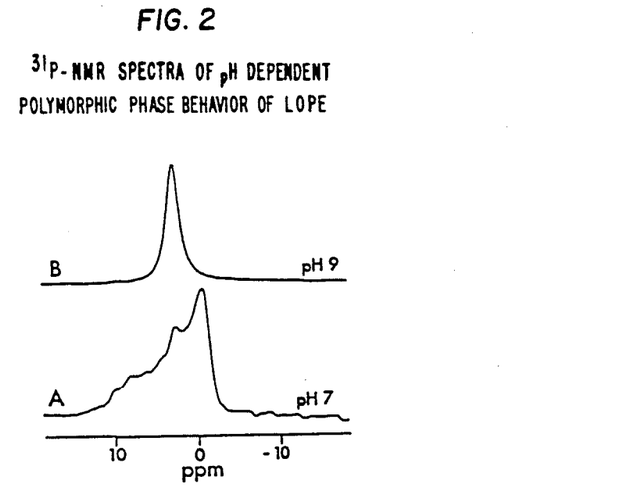
FIG. 2 are $^{31}$P-NMR spectra showing the effect of pH variation on the polymorphic phase behavior of LOPE.

We have found that 1-oleoyl lysophosphatidylethanolamine (LOPE, or sn-1-18:1$_{cis}$-PE) exhibits a lamellar phase at physiological pH rather than the micellar arrangement of other lysophospholipids. LOPE, however, exhibits a micellar state at higher pH (i.e., at about 8.5 or higher) which promotes micellar solubilization of hydrophobic substance under such conditions. This polymorphic phase behavior from micellar to bilayer states is substantiated by: (a) $^{31}$P-NMR spectra, which correspond to a lamellar configuration at pH 7 at temperatures of $-20°$ C. to $90°$ C., in contrast to lysophosphatidylcholine which is micellar (FIG. 1); (b) x-ray diffraction patterns of LOPE, in which the x-ray scatter forms equidistantly spaced rings, indicative of a lamellar organization; (c) freeze fracture micrographs which show the unilamellar nature of LUVETS produced at pH 7.0; and (d) $^{31}$P-NMR spectra that show isotropic motional averaging at pH 9.0, indicative of a micellar structure (FIG. 2). This polymorphic phase behavior allows micellar solubilization of a hydrophobic material at a pH of about 8.5, and bilayer formation at lower pH.

Figure 3:
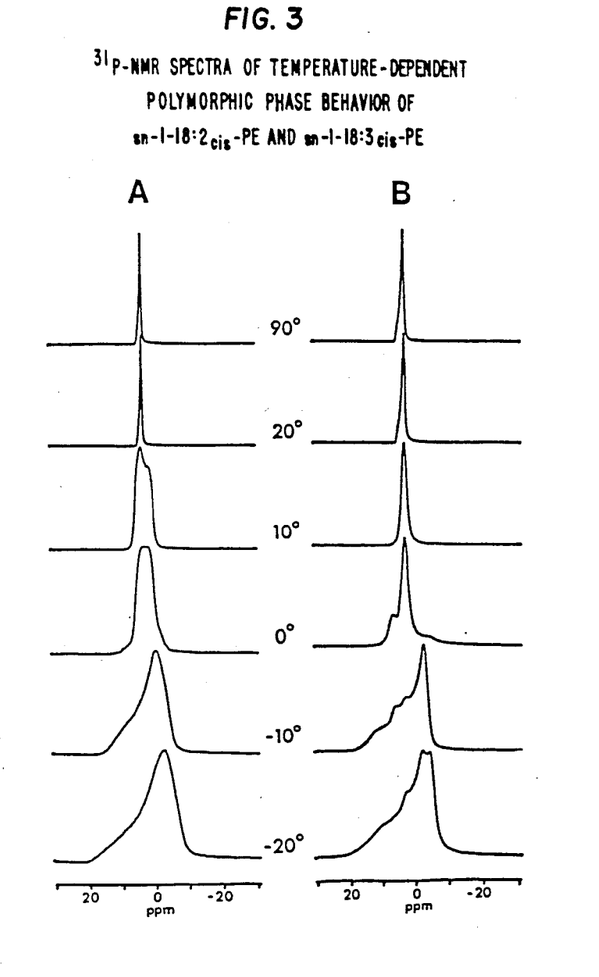
FIG. 3 are $^{31}$P-NMR spectra showing the effect of temperature variation on the polymorphic phase behavior of (A) sn-1-18:$2_{cis}$-PE and (B) sn-1-18:$3_{cis}$-PE.

We have also found that lysophosphatidylethanolamines having 2 or 3 double bonds such as sn-1-18:2$_{cis}$-PE and sn-1-18:3$_{cis}$-PE, respectively, exhibit polymorphic phase behavior in response to temperature variation. Below $0°$ C., both lipids give rise to $^{31}$P-NMR spectra indicative of overall lamellar organization indicated by a low field shoulder followed by a peak (FIG. 3). Both sn-1-18:2$_{cis}$-PE and sn-1-18:3$_{cis}$-PE show a hexagonal structure at $0°-1°$ C. However, at $10°-20°$ C. and above, both lipids are in the (inverted) micelle or H$_I$ state.

In the present invention, a lipid film and hydrophobic material are mixed in an aqueous medium resulting in solubilization of the hydrophobic material. This solubilization may be achieved by several methods. In the case where LOPE is the solubilizing lipid used, the hydrophobic material is combined with LOPE in an amount sufficient to solubilize it, and both dried to a film in a receptacle, from an organic solvent. Suitable organic solvents are those with a variety of polarities and dielectric properties, including chloroform, acetone, methylene chloride, diethyl and petroleum ethers, and mixtures of chloroform and methanol. All of the above-mentioned solvents will dissolve the phospholipids. The dry film is then hydrated with an aqueous medium at pH of between about 8.2 and about 14.0. Alternatively, a dry film of LOPE may be hydrated with an aqueous medium at pH of between about 8.2 and 14.0, followed by addition of the hydrophobic material. Lastly, an aqueous medium at pH of between about 8.2 and about 14.0 containing a hydrophobic material may be used to hydrate a dry film of LOPE. The hydrophobic material may be a bioactive agent.

In the preferred embodiment, lipid and hydrophobic material are dried under vacuum from chloroform to a thin film. The dried film is then hydrated with an aqueous buffer such as borate, HEPES, or potassium glutarate (KGlu) at pH 8.5-14.0; most preferably about pH 8.5. In general, in the 8.5-14.0 pH range, lysophosphatidylethanolamine assumes its micellar state. At pH of about 8.0 and lower, LOPE is in a lamellar state. The hydrophobic material is rehydrated with the lipid in an aqueous medium with agitation and/or vertical mixing. The concentration of hydrophobic material can preferably range from about 5-25 mg/ml of buffer. The LOPE dispersion was held at $4°$ C. for 2-3 hours to favor micellization. This dispersion is optionally then subjected to up to about 10 repeated extrusions at pressures of about 700 psi using an extrusion apparatus; this method and "LUVET" apparatus described in a copending application, Ser. No. 622,690, filed June 20, 1984, Pieter R. Cullis et. al., "Extrusion Technique for Producing Unilamellar Vesicles", relevant portions of which are incorporated herein by reference. The samples were held at about $20°-30°$ C., preferably about $25°$ C. for 16-18 hours to confirm complete solubilization, evidenced by lack of precipitation. The solubilized product can be used as an injectable product administered, for example, intravenously, intramuscularly, or subcutaneously, in a subject including mammals such as humans. The product is best used in the form of a sterile aqueous solution which may contain other solutes, for example, enough salts or glucose to make the solution isotonic.

In the cases where sn-1-18:2$_{cis}$-PE or sn-1-18:3$_{cis}$-PE's are the solubilizing lipids used, the hydrophobic material may be combined with the lipid in an amount sufficient to solubilize it, and both dried to a film in a receptacle, from organic solvent. The dry film may then be hydrated with an aqueous medium at pH between about 6.0 and 8.0 and held at a temperature from about $-90°$ C., to $0°$ C., preferably about $-20°$ C., which favors the lamellar phase of the lipid. Alternatively, a dry lipid film may be hydrated with an aqueous medium at pH of between about 6.0 and 8.0 followed by addition of or combined with the hydrophobic material. The solubilized product may be stored at this reduced temperature, in lamellar phase lipid for purposes of enhancing shelf life.

MATERIALS AND METHODS

Dioleoyl phosphatidylethanolamine (DOPE) was prepared from dioleoyl PC according to established procedures, Confurius, P. et al., *Biophys. Biochem. Acta.*, 488, 36-42 (1977). Lysophosphatidylethanolamine was prepared according to the following protocol: 500 mg DOPE was dissolved in 50 ml anhydrous diethyl ether to which was added 10 ml 0.5M Tris/HCl buffer (pH 7.4), 10 ml of 2.5 mM CaCl$_2$ and 100 mg of *Crotalus adamanteus* venom (Sigma Chemical Co., St. Louis, MO). The reaction vessel was flushed with nitrogen, sealed, covered with aluminum foil, and stirred vigorously at room temperature. The mixture was rotoevaporated under reduced pressure to remove the diethyl ether and the aqueous phase extracted with chloroform methanol 2:1 v/v followed by chloroform. The preparation was purified by liquid chromatography using a Waters Prep 500 LC unit. Purity was further verified by H-NMR.

The present invention is exemplified by the following Examples, but the scope of the invention is not limited thereto.

EXAMPLE 1

Fifty μmol of LOPE combined with 5 mg of 21-acetoxypregnenolone (Sigma Chemical Co., St. Louis, MO) was rotoevaporated to a dried film from chloroform onto the inner sides of a test tube. One ml of borate buffer (100 mM NaHCO$_3$, 50 mM borate), pH 8.5, was added to the tube and the lipid dispersed by vortexing. After dispersion by vortexing, the preparations were left to stand at $4°$ C. for 2-3 hours. The dispersions were then transferred into the pressure chamber of the LUVET apparatus, equipped with two stacked 100 nm polycarbonate filters. Positive pressure was applied to the chamber by way of a standard nitrogen cylinder at 500 psi. The pressure was adjusted within the 200–900 psi range to allow complete extrusion of the sample without the membrane filter clogging. Application of pressure results in the extrusion of the sample through the filters. Each sample was extruded a total of ten times.

The above procedures were repeated using 10, 15, 20, and 25 mg of 21-acetoxypregnenolone.

The samples were left at 25° C. for 16–18 hours, after which time all samples appeared clear; viscosity increasing with increasing 21-acetoxyprepnenolone content.

EXAMPLE 2

The procedures and materials of Example 1 were employed using LOPE and DOPC in a 1:1 molar ratio to solubilize 10 mg of 21-acetoxypregnenolone. Following the LUVET treatment, the solution was allowed to stand for 16–18 hours at 25° C., and a further LUVET filtration employing a 50 nm filter system at a pressure of 200 psi was performed. Following this treatment, no particulate material was observed on the filter, and the preparation appeared translucent. Attempts to solubilize 20 mg of steroid in 1.0 ml of buffer were unsuccessful.

EXAMPLE 3

Hemolytic properties of 1-oleoyl lysophosphatidylethanolamine (LOPE) were tested at both pH 7.0 and 8.5, and compared to those of 1-oleoyl lysophosphatidylcholine (LOPC) and dipalmitoylphosphatidylethanolamine (DPPE). LOPE, LOPC, and DPPE stock solutions were made at 12–13 mg/ml in 50 mM borate buffer at pH 7.0 and 8.5. Following the additions of 0.1 ml volumes of stock solution of one of these compounds to 1.0 ml aliquots of heparinized whole blood, hemolytic activities were assayed by spectrophotometric measurement of the centrifuged supernatants at 550 nm.

Figure 4:
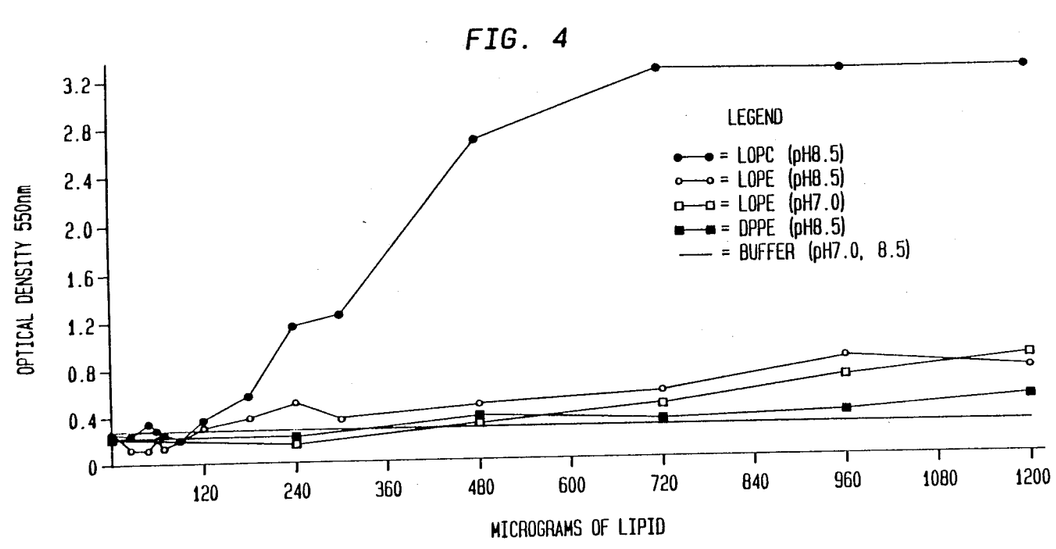
FIG. 4 is a graph depicting the hemolytic properties of various phospholipids.
Figure 5:
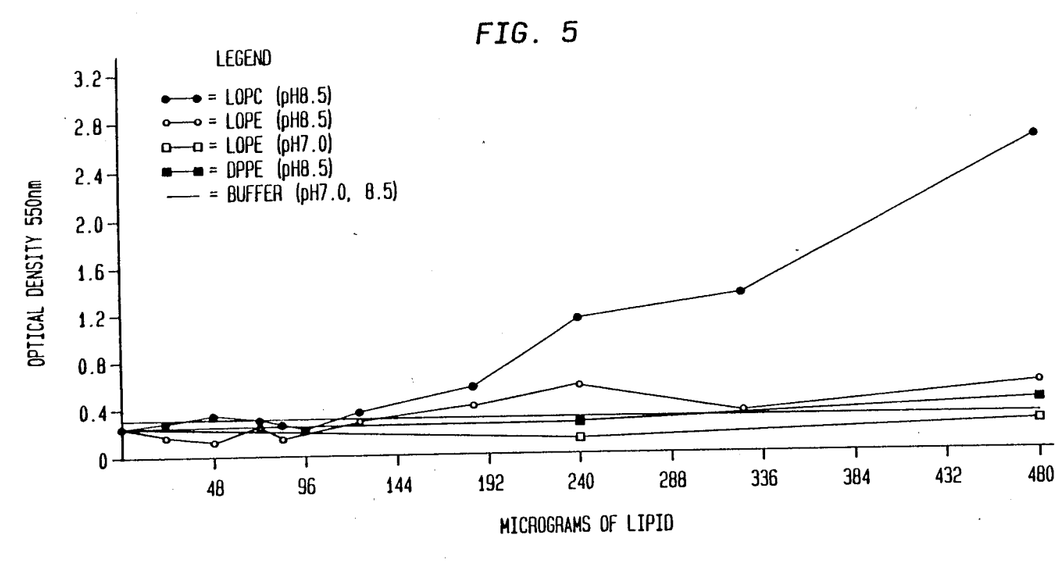
FIG. 5 is an expended scale of hemolytic properties of various phospholipids.

FIG. 4 shows the reduced hemolytic activity of LOPE at both pH 7.0 and 8.5 as compared to LOPC, when added to whole blood. LOPC produced the greatest amount of red blood cell lysis, liberating the most hemoglobin. High concentrations of LOPE produced lysis as compared to DPPE, which caused minimal lysis (FIG. 5). Control experiments with borate buffer alone at both pH 7.0 and 8.5 produced no lysis.

EXAMPLE 4

Fifty μmol of sn-1-18:2$_{cis}$-PE combined with 5 mg of 21-acetoxypregnenolone is rotoevaporated to a dry film from chloroform onto the inner sides of a test tube. One ml of borate buffer, pH 7.0, is added to the tube and the lipid dispersed by vortical mixing. After dispersion, the suspension is cooled to −20° C., and transferred into the pressure chamber of the LUVET and extruded using the procedures of Example 1.

We claim:

1. A method of solubilizing a hydrophobic material comprising the steps of:
   (a) removing an organic solvent in which a composition comprising a hydrophobic-material-solubilizing effective amount of a lysophosphatidylethanolamine of the formula:

or and a hydrophobic material are dissolved to obtain a film;
   (b) hydrating the film with an aqueous medium at pH of between about 8.5 and about 14.0; and
   (c) admixing the aqueous medium and the hydrated film comprising the hydrophobic material and the lysophosphatidylethanolamine.
   wherein R is a hydrocarbon chain having between about 11 and 21 carbon atoms and 1 double bond.

2. The method according to claim 1 wherein the hydrophobic material is a bioactive agent.

3. The method according to claim 1 wherein the aqueous medium is at pH of about 8.5.

4. The method according to claim 1 wherein the lysophosphatidylethanolamine has formula I.

5. The method according to claim 4 wherein R has between about 13 to 19 carbon atoms.

6. The method according to claim 4 wherein R has between about 15 to 17 carbon atoms, and 1 double bond.

7. The method according to claim 4 wherein $RCO_2$ is 1-oleoyl.

8. The method according to claim 1 wherein $RCO_2$ is 1-oleoyl.

9. The method according to claim 1 wherein the aqueous medium comprises aqueous buffer.

10. The method according to claim 1 comprising the additional step of: (d) filtering the product of step (c).

11. The method according to claim 10 comprising the additional step of administering parenterally the product of step (c).

12. The method according to claim 1 wherein the composition additionally comprises an unsaturated phospholipid.

13. The method according to claim 12 wherein the unsaturated phospholipid comprises at least one unsaturated fatty acid chain of between about 12 and 22 carbon atoms and 1 to 6 double bonds.

14. The method according to claim 13 wherein the unsaturated phospholipid has between about 16 to 20 carbon atoms and 1 to 3 double bonds.

15. The method according to claim 13 wherein the second fatty acid chain of the unsaturated phospholipid has between about 12 and 22 carbon atoms and 0 to 6 double bonds.

16. The method according to claim 15 wherein the second fatty acid chain of the unsaturated phospholipid has between about 16 and 20 carbon atoms and 1 to 3 double bonds.

17. The method according to claim 13 wherein the unsaturated phospholipid is selected from the group consisting of egg phosphatidylcholine, soy phosphatidylcholine, and dioleoylphosphatidylcholine.

18. The method according to claim 13 comprising the additional step of (d) filtering the product of step (c).

19. The method according to claim 18 comprising the additional step of administering parenterally to a mammal the product of the filtering step.

20. A method of solubilizing a hydrophobic material comprising the steps of:
   (a) removing an organic solvent in which a composition comprising a hydrophobic-material-solubilizing effective amount of lysophosphatidylethanolamine of the formula:

or and a hydrophobic material are dissolved to obtain a film;
  (b) hydrating the film with an aqueous medium at pH of between about 6.0 and about 8.0;
  (c) admixing the aqueous medium and the hydrated film comprising the hydrophobic material and the lysophosphatidylethanolamine; and
  (d) cooling the dispersed lipid in aqueous medium to a temperature below about 20° C.;
  wherein R is a hydrocarbon chain having between about 11 and 21 carbon atoms and about 2 to 6 double bonds.

21. The method according to claim 20 wherein the hydrophobic material is a bioactive agent.

22. The method according to claim 20 wherein the aqueous medium is at pH of about 7.0.

23. The method according to claim 20 wherein the lysophosphatidylethanolamine has formula I.

24. The method according to claim 23 wherein R has between about 13 to 19 carbon atoms.

25. The method according to claim 23 wherein R has between about 15 to 17 carbon atoms, and 2 or 3 double bonds.

26. The method according to claim 23 wherein $RCO_2$ is 1-oleoyl.

27. The method according to claim 20 wherein $RCO_2$ is 1-oleoyl.

28. The method according to claim 20 wherein the aqueous medium comprises aqueous buffer.

29. The method according to claim 20 comprising the additional step of: (e) filtering the product of step (d).

30. The method according to claim 20 wherein the composition additionally comprises an unsaturated phospholipid.

31. The method according to claim 30 wherein the unsaturated phospholipid comprises at least one unsaturated fatty acid chain of between about 12 and 22 carbon atoms and 1 to 6 double bonds.

32. The method according to claim 31 wherein the unsaturated phospholipid has between about 16 to 20 carbon atoms and 1 to 3 double bonds.

33. The method according to claim 32 wherein the second fatty acid chain of the unsaturated phospholipid has between about 12 and 22 carbon atoms and 0 to 6 double bonds.

34. The method according to claim 33 wherein the second fatty acid chain of the unsaturated phospholipid has between about 16 and 20 carbon atoms and 1 to 3 double bonds.

35. The method according to claim 34 wherein the unsaturated phospholipid is selected from the group consisting of egg phosphatidylcholine, soy phosphatidylcholine, and dioleoylphosphatidylcholine.

36. The method according to claim 30 comprising the additional step of: (e) filtering the product of step (d).

37. A composition comprising an aqueous micellar solution at between about pH 8.5 to 14.0 of a hydrophobic material and a lysophospholipid of the formula:

or wherein R is a hydrocarbon chain having between about 11 and 21 carbon atoms and 1 double bond.

38. The composition according to claim 37 wherein the aqueous solution is at a pH of about 8.5.

39. The composition of claim 37 wherein the lysophosphatidylethanolamine has formula I.

40. The composition of claim 37 wherein R has between about 13 to 19 carbon atoms.

41. The composition of claim 37 wherein R has between about 15 and 17 carbon atoms.

42. The composition of claim 37 wherein R has 1 to 2 double bonds.

43. The composition of claim 37 where $RCO_2$ is 1-oleoyl.

44. The composition of claim 37 wherein the hydrophobic material is a bioactive agent.

45. The composition of claim 37 wherein the aqueous solution comprises aqueous buffer.

46. The composition according to claim 37 additionally comprising an unsaturated phospholipid.

47. The composition of claim 46 wherein the unsaturated phospholipid comprises at least one unsaturated fatty acid chain of between about 12 and 22 carbon atoms and 1 to 6 double bonds.

48. The composition of claim 46 wherein the second fatty acid chain of the unsaturated phospholipid comprises between about 12 and 22 carbon atoms and 0 to 6 double bonds.

49. The composition of claim 46 wherein the unsaturated phospholipid has between about 16 to 20 carbon atoms and 1 to 3 double bonds.

50. The composition of claim 46 wherein the unsaturated phospholipid is selected from the group consisting of egg phosphotidylcholine, soy phosphatidylcholine, and dioleoylphosphatidylcholine.

51. A composition comprising an aqueous micellar solution of between about pH 6.0 to 8.0 of a hydrophobic material and a lysophospholipid of the formula:

or wherein R is a hydrocarbon chain having between about 11 and 21 carbon atoms and about 2 to 6 double bonds, and wherein the temperature of the composition is between about −20° C. and about 0° C.

52. The composition according to claim 51 wherein the aqueous solution is at a pH of about 7.0.

53. The composition of claim 51 wherein the lysophosphatidyletanolamine has formula I.

54. The composition of claim 51 wherein R has between about 13 to 19 carbon atoms.

55. The composition of claim 51 wherein R has between about 15 and 17 carbon atoms, and 2 or 3 double bonds.

56. The composition of claim 51 where $RCO_2$ is 1-oleoyl.

57. The compositions of claim 51 wherein the hydrophobic material is a bioactive agent.

58. The compositions of claim 51 wherein the aqueous solution comprises aqueous buffer.

59. The composition according to claim 51 additionally comprising an unsaturated phospholipid.

60. The composition of claim 59 wherein the unsaturated phospholipid comprises at least one unsaturated fatty acid chain of between about 12 and 22 carbon atoms and 1 to 6 double bonds.

61. The composition of claim 59 wherein the second fatty acid chain of the unsaturated phospholipid comprises between about 12 and 22 carbon atoms and 0 to 6 double bonds.

62. The composition of claim 59 wherein the unsaturated phospholipid has between about 16 to 20 carbon atoms and 1 to 3 double bonds.

63. The composition of claim 59 wherein the unsaturated phospholipid is selected from the group consisting of egg phosphotidylcholine, soy phosphatidylcholine, and dioleoylphosphataidylcholine.

64. A method of solubilizing a hydrophobic material comprising the steps of:
(a) removing an organic solvent in which a composition comprising a hydrophobic-material-solubilizing effective amount of a lysophosphatidylethanolamine of the formula:

$$H_2C(O_2CR)CH(OH)CH_2OP(O)_2OCH_2CH_2NH_3 \quad I$$

or $$H_2C(OH)CH(O_2CR)CH_2OP(O)_2OCH_2CH_2NH_3 \quad II$$

is dissolved to obtain a film,
(b) hydrating the film with an aqueous medium at pH of between about 8.5 and about 14.0; and
(c) admixing the hydrophobic material with the hydrated film of step (b), wherein R is a hydrocarbon chain having between about 11 and 21 carbon atoms and 1 double bond.

65. The method according to claim 64 wherein the hydrophobic material is a bioactive agent.

66. The method according to claim 64 wherein the aqueous medium is at pH of about 8.5.

67. The method according to claim 64 wherein the lysophosphatidylethanolamine has formula I.

68. The method according to claim 67 wherein R has between about 13 to 19 carbon atoms.

69. The method according to claim 68 wherein R has between about 15 to 17 carbon atoms, and 1 double bond.

70. The method according to claim 67 wherein $RCO_2$ is 1-oleoyl.

71. The method according to claim 64 wherein $RCO_2$ is 1-oleoyl.

72. The method according to claim 64 wherein the aqueous medium comprises aqueous buffer.

73. The method according to claim 64 comprising the additional step of: (d) filtering the product of step (c).

74. The method according to claim 73 comprising the additional step of administering parenterally the product of step (b).

75. The method according to claim 64 wherein the composition additionally comprises an unsaturated phospholipid.

76. The method according to claim 75 wherein the unsaturated phospholipid comprises at least one unsaturated fatty acid chain of between about 12 and 22 carbon atoms and 1 to 6 double bonds.

77. The method according to claim 76 wherein the unsaturated phospholipid has between about 16 to 20 carbon atoms and 1 to 3 double bonds.

78. The method according to claim 76 wherein the second fatty acid chain of the unsaturated phospholipid has between about 12 and 22 carbon atoms and 0 to 6 double bonds.

79. The method according to claim 78 wherein the second fatty acid chain of the unsaturated phospholipid has between about 16 and 20 carbon atoms and 1 to 3 double bonds.

80. The method according to claim 76 wherein the unsaturated phospholipid is selected from the group consisting of egg phosphatidylcholine, soy phosphatidylcholine, and dioleoylphosphatidylcholine.

81. The method according to claim 76 comprising the additional step of filtering the product of step (c).

82. The method according to claim 81 comprising the additional step of administering parenterally to a mammal the product of the filtering step.

83. A method of solubilizing a hydrophobic material comprising the steps of:
(a) removing an organic solvent in which a composition comprising a hydrophobic-material-solubilizing effective amount of lysophosphatidylethanolamine of the formula:

$$H_2C(O_2CR)CH(OH)CH_2OP(O)_2OCH_2CH_2NH_3 \quad I$$

or $$H_2C(OH)CH(O_2CR)CH_2OP(O)_2OCH_2CH_2NH_3 \quad II$$

is dissolved to obtain a film;
(b) hydrating the film with an aqueous medium at pH of between about 6.0 and about 8.0;
(c) admixing the hydrophobic material with the hydrated film of step (b); and
(d) cooling the dispersed lipid in aqueous medium to a temperature below about 0° C;
wherein R is a hydrocarbon chain having between about 11 and 21 carbon atoms and about 2 to 6 double bonds.

84. The method according to claim 83 wherein the hydrophobic material is a bioactive agent.

85. The method according to claim 83 wherein the aqueous medium is at pH of about 7.0.

86. The method according to claim 83 wherein the lysophosphatidylethanolamine has formula I.

87. The method according to claim 86 wherein R has between about 13 to 19 carbon atoms.

88. The method according to claim 86 wherein R has between about 15 to 17 carbon atoms, and 2 or 3 double bonds.

89. The method according to claim 86 wherein $RCO_2$ is 1-oleoyl.

90. The method according to claim 83 wherein $RCO_2$ is 1-oleoyl.

91. The method according to claim 83 wherein the aqueous medium comrises aqueous buffer.

92. The method according to claim 83 comprising the additional step of: (d) filtering the product of step (c).

93. The method according to claim 83 wherein the composition additionally comprises an unsaturated phospholipid.

94. The method according to claim 93 wherein the unsaturated phospholipid comprises at least one unsaturated fatty acid chain of between about 12 and 22 carbon atoms and 1 to 6 double bonds.

95. The method according to claim 93 wherein the unsaturated phospholipid has between about 16 to 20 carbon atoms and 1 to 3 double bonds.

96. The method according to claim 94 wherein the second fatty acid chain of the unsaturated phospholipid has between about 12 and 22 carbon atoms and 0 to 6 double bonds.

97. The method according to claim 95 wherein the second fatty acid chain of the unsaturated phospholipid has between about 16 and 20 carbon atoms and 1 to 3 double bonds.

98. The method according to claim 97 wherein the unsaturated phospholipid is selected from the group consisting of egg phosphatidylcholine, soy phosphatidylcholine, and dioleoylphosphatidylcholine.

99. The method according to claim 93 comprising the additional step of filtering the product of step (c).

* * * * *